US00PP28572P2

(12) United States Plant Patent
Probst

(10) Patent No.: US PP28,572 P2
(45) Date of Patent: Oct. 24, 2017

(54) ***COREOPSIS* PLANT NAMED 'SOPHIA'**

(50) Latin Name: ***Coreopsis* hybrid**
Varietal Denomination: Sophia

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 138 days.

(21) Appl. No.: 14/756,564

(22) Filed: Sep. 17, 2015

(51) Int. Cl.
*A01H 5/02* (2006.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of hybrid *Coreopsis* named 'Sophia' characterized by its compact plant habit reaching an average of 45 cm in height and 45 cm in width, its near sterility with a floriferous and long bloom season that does not require deadheading with bloom commences in late June and lasts until frost in Kensington, Conn., its medium sized inflorescences with tube-shaped ray florets that are light yellow in color, its lack of requirement for vernalization to initiate flowering, its cold hardiness to at least U.S.D.A. Zone 5, and its resistance to powdery mildew and leaf spot.

2 Drawing Sheets

Botanical classification: *Coreopsis* hybrid.
Variety denomination: 'Sophia'.

CROSS REFERENCE TO A RELATED APPLICATION

This application is co-pending with a U.S. Plant Patent Application filed for a plant derived from the same breeding program that is entitled *Coreopsis* Plant Named 'Lauren' (U.S. Plant patent application Ser. No. 14,757,585).

BACKGROUND OF THE INVENTION

The present invention relates to a new and distinct cultivar of a plant botanically of hybrid origin and known as *Coreopsis*. The new cultivar will be referred to hereafter by its cultivar name 'Sophia'. 'Sophia' is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and are cold hardy at least to U.S.D.A. Zone 5 in a wide range of flower colors and plant forms on plants that do not require vernalization to initiate flowering.

The Inventor made a controlled cross in August of 2011 in his test garden in Hubbardston, Mass. between an unnamed proprietary plant from the Inventor's breeding program, reference no. G 08-8 (not patented), as the female parent and pollen that was pooled from a variety of unnamed, proprietary plants (not patented) from his breeding program as the male parent (all with tube-shaped ray florets). The exact male parentage is therefore unknown. 'Sophia' was selected in September of 2012 as a single unique plant amongst the resulting seedlings.

Asexual propagation of the new cultivar was first accomplished by stem cuttings in Kensington, Conn. in September of 2012 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Sophia' as unique cultivar of *Coreopsis*.

1. 'Sophia' exhibits a compact plant habit reaching an average of 45 cm in height and 45 cm in width.
2. 'Sophia' is nearly sterile and exhibits a floriferous and long bloom season that does not require deadheading; bloom commences in late June and lasts until frost in Kensington, Conn.
3. 'Sophia' exhibits medium sized inflorescences with tube-shaped ray florets that are light yellow in color.
4. 'Sophia' does not require vernalization to initiate flowering.
5. 'Sophia' exhibits cold hardiness to at least U.S.D.A. Zone 5.
6. 'Sophia' exhibits resistance to powdery mildew and leaf spot.

The female parent of 'Sophia', G 08-8, differs from 'Sophia' in having inflorescences with ray florets that are flat in aspect and not tube-shaped. 'Sophia' can be compared to the *Coreopsis* cultivars 'Jethro Tull' (U.S. Plant Pat. No. 18,789), 'Galaxy' (U.S. Plant Pat. No. 21,999) and 'Lauren'. 'Jethro Tull' is similar to 'Sophia' in having inflorescences with tube-shaped ray florets. 'Jethro Tull' differs from 'Sophia' in having inflorescences that are gold in color, in having a less dependable perennial habit, in being prone to powdery mildew when grown under similar conditions in Hubbardston, Mass., and in requiring vernalization to initiate flowering. 'Galaxy' is similar to 'Sophia' in having inflorescences that are light yellow in color. 'Galaxy' differs from 'Sophia' in having semi-double inflorescences with ray florets that are flat in aspect and not tube-shaped. 'Lauren' is similar to 'Sophia' in having medium sized light yellow inflorescences, similar cold hardiness and disease resistance, and in lacking a requirement for vernalization. 'Lauren' differs from 'Sophia' in lacking tube shaped ray florets and in having a more densely bushy and less upright plant habit.

BRIEF DESCRIPTION OF THE DRAWINGS

The accompanying colored photographs illustrate the overall appearance and distinct characteristics of the new *Coreopsis*. The photographs were taken of a three month-old plant of 'Sophia' as grown in a one-gallon container from a 30-cell plug in New Braintree, Mass.

The photograph in FIG. 1 provides a side view of a plant of 'Sophia' in bloom.

Figure 1:
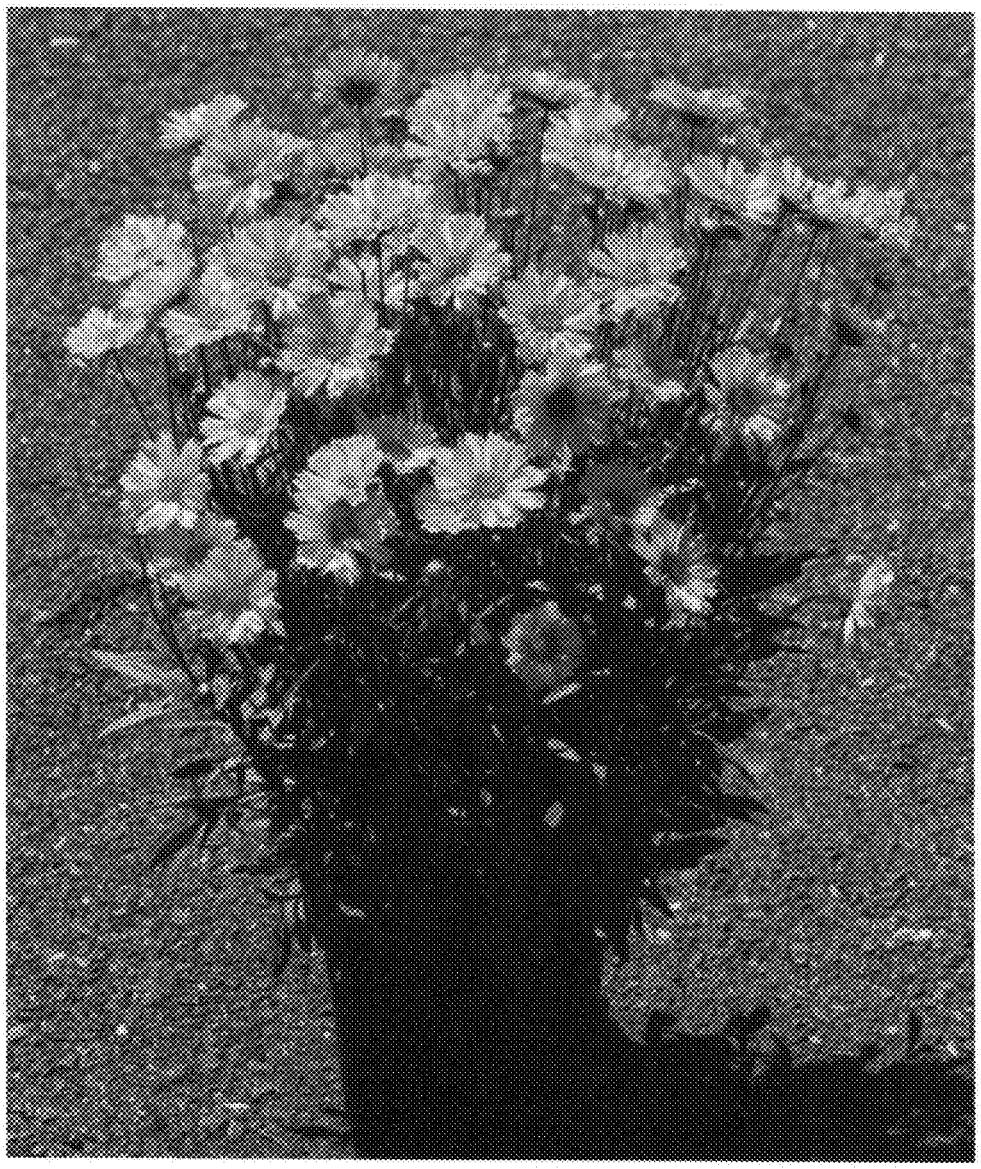
Figure 2:
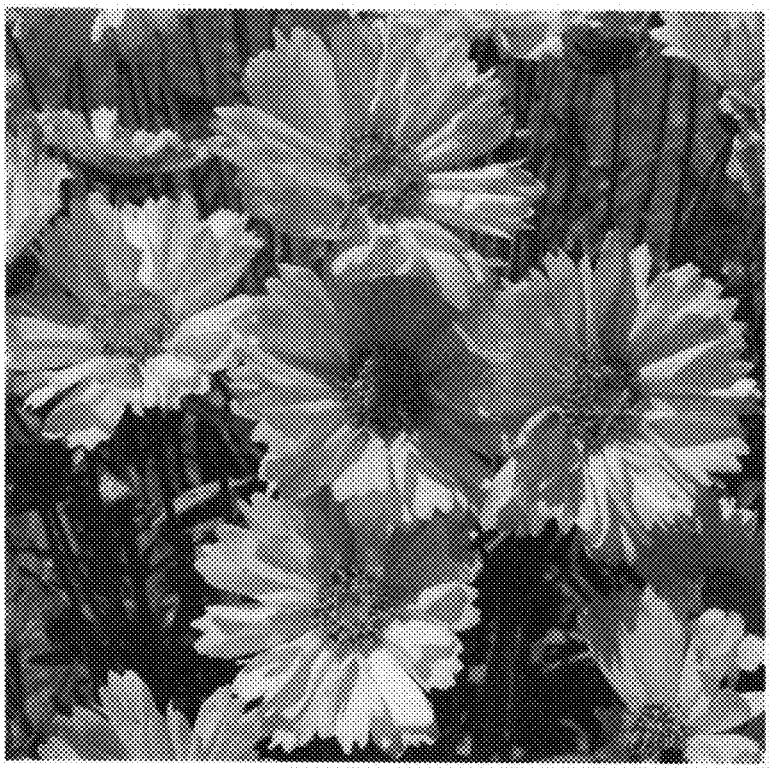

The photograph in FIG. 2 provides a view of several inflorescences of 'Sophia'.

Figure 3:
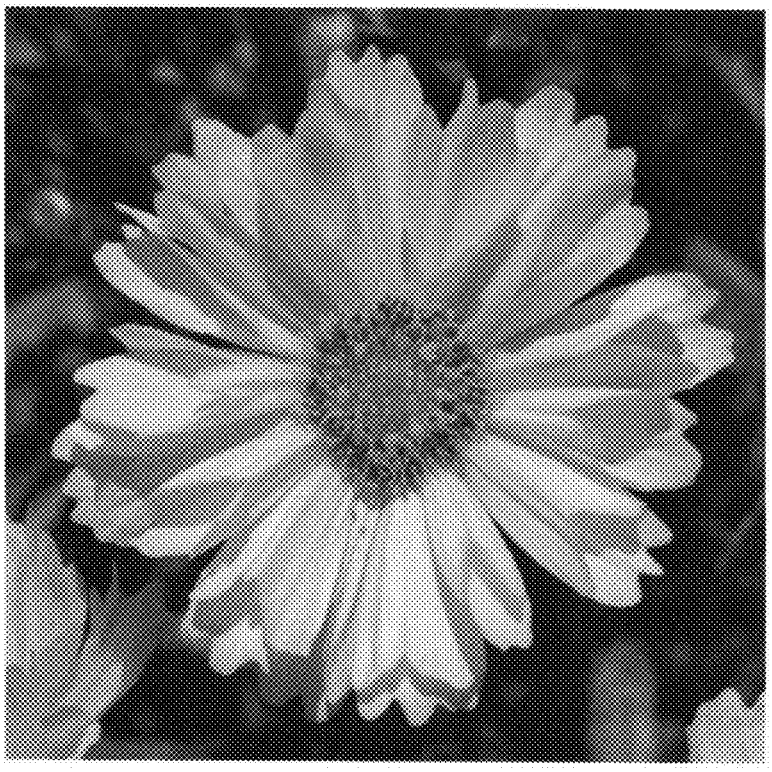

The photograph in FIG. 3 provides a close-up view of an inflorescence of 'Sophia'.

The colors in the photograph may differ slightly from the color values cited in the detailed botanical description, which accurately describe the colors of the new *Coreopsis*.

DETAILED BOTANICAL DESCRIPTION

The following is a detailed description of three month-old plants of 'Sophia' as grown outdoors in one-gallon containers from 128-cell plugs in Kensington, Conn. The phenotype of the new cultivar may vary with variations in environmental, climatic, and cultural conditions, as it has not been tested under all possible environmental conditions. The color determination is in accordance with The 2007 Royal Horticultural Society Colour Chart of The Royal Horticultural Society, London, England, except where general color terms of ordinary dictionary significance are used.

General description:

*Blooming period*.—Blooms from late June and lasts until frost in Kensington, Conn.

*Plant type*.—Herbaceous perennial.

*Plant habit*.—Compact and upright.

*Height and spread*.—An average of 45 cm in height and 45 cm in width.

*Cold hardiness*.—At least in U.S.D.A. Zone 5.

*Diseases resistance*.—Has been observed to be resistant to powdery mildew (*Podosphaera macularis*) and leaf spot (*Pseudomonas cichorii*).

*Root description*.—Fibrous when young, becoming fleshy with age, 162D in color.

*Root development*.—Roots initiate in 6 to 8 days and fully develop in a 128-cell plug in about 28 days with bottom heat and rooting hormone at optimal times of the year.

*Propagation*.—Division and stem cuttings (preferred).

*Growth rate*.—Vigorous, but stays compact.

Stem description:

*Shape*.—Oval, ridged.

*Stem color*.—Young; 143B to 143C, mature bark; 134B suffused with 199C.

*Stem size*.—Main and secondary stems; an average of 20 cm in length and 4.5 mm in width, tertiary stems; an average of 15 cm in length and 3 mm in width.

*Stem surface*.—Glabrous.

*Stem aspect*.—Upright.

*Stem strength*.—Strong.

*Branching habit*.—Well-branched, an average of 1 main branches, 6 secondary branches per main stem, 2 tertiary stems.

*Internode length*.—An average of 2.8 cm.

Foliage description:

*Leaf division*.—Simple.

*Leaf margins*.—Entire to trifid.

*Leaf size*.—Variable, up to 9.5 cm in length and 1.6 cm in width when entire, up to 11 cm in length and 5 cm in width when trifid.

*Leaf shape*.—Oblanceolate when entire, oblanceolate lobes when trifid.

*Leaf base*.—Truncate to clasping.

*Leaf apex*.—Acute.

*Leaf venation*.—Pinnate, inconspicuous, matches leaf color on upper and lower surface.

*Leaf attachment*.—Sessile.

*Leaf arrangement*.—Opposite.

*Leaf surface*.—Upper and lower surface slightly hirsute and dull.

*Leaf color*.—Young and mature upper surface; 137A, young and mature lower surface; 138A.

Inflorescence description:

*Inflorescence type*.—Composite with overlapping tube-shaped ray florets surrounding disk florets in the center.

*Lastingness of inflorescence*.—8 to 10 days until senescence of ray flowers, longer in cool temperatures, bracts and disk flowers are persistent.

*Fragrance*.—Very slight sweet honey scent.

*Quantity of inflorescences*.—An average of 20 per main branch.

*Inflorescence size*.—An average of 2 cm in depth and up to 5 cm in diameter.

*Inflorescence buds*.—Average of 8 mm in depth and in diameter, spherical in shape with a flattened top, color; a blend of 143C and 153A.

*Peduncle*.—Average of 8 cm in length and 2 mm in width, ridged, glabrous surface, strong, 143B to 143C.

*Sepals*.—An average of 8,9 mm in length and 2 mm in width, color; 137A with base 143C.

Involucral bracts:

*Bract number*.—8, 4 outer bracts and 4 inner bracts.

*Bract arrangement*.—Bracts surround receptacle in a campanulate form, held close to lower surface of ray florets.

*Bract size*.—An average of 9 mm in length and 5 mm in width.

*Bract color*.—Transluscent; apex, 9B with narrow parallel lines N199A and base 143C.

*Bract texture*.—Outer and inner surface; glabrous and satiny.

*Bract apex*.—Acute.

*Bract base*.—Truncate.

*Bract margins*.—Entire.

*Bract shape*.—Ovate.

Ray florets (sterile):

*Number*.—An average of 17 arranged primarily in one row.

*Shape*.—Obovate to oblanceolate, tube-shaped.

*Size*.—An average of 2 cm in length and 1 cm in width and tubes 5 mm in width.

*Apex*.—3 notched.

*Base*.—Cuneate.

*Margins*.—Entire with apex notched.

*Aspect*.—Held upward and outward.

*Texture*.—Glabrous on upper and lower surface.

*Color*.—When opening and when fully open, inner and outer surface; 5A to 5B.

Disk flowers (perfect):

*Shape*.—Tubular, corolla is fused, flared at apex.

*Number*.—About 50.

*Size*.—About 5 mm in length and 1.5 mm in width.

*Color*.—En masse; 13B, corolla tube; 13C to 13D, apex; 13B.

*Receptacle*.—About 5 mm in diameter and 2 mm in depth, color; 145C to 145D.

Reproductive organs:

*Presence*.—Disk flowers are perfect, ray flowers are sterile.

*Gynoecium*.—1 Pistil, 5 mm in length, style is very fine, translucent and 154C in color, two-lobed stigma is 13A in color, ovary is 1.5 mm in length, 1 mm in width, inferior, and 145D in color.

*Androcoecium*.—3 stamens, fused into tube surrounding style, 1.5 mm in length and 0.2 mm in width, about 175A in color, pollen is moderate in quantity and 15A in color.

*Fruit/seed*.—Nearly sterile, no fruit or seed development has been observed to date.

It is claimed:

1. A new and distinct cultivar of *Coreopsis* plant named 'Sophia' as herein illustrated and described.

* * * * *